(12) United States Patent
Hurd

(10) Patent No.: US 7,137,961 B2
(45) Date of Patent: Nov. 21, 2006

(54) METHOD AND PORTABLE APPARATUS FOR SPINAL ADJUSTMENT

(76) Inventor: Neal Russell Hurd, N8401 Klappstein Rd., Portage, WI (US) 53901

( * ) Notice: Subject to any disclaimer, the term of this patent is extended or adjusted under 35 U.S.C. 154(b) by 553 days.

(21) Appl. No.: 10/041,445

(22) Filed: Jan. 8, 2002

(65) Prior Publication Data

US 2003/0130696 A1 Jul. 10, 2003

(51) Int. Cl.
*A61F 5/00* (2006.01)
(52) U.S. Cl. ............... 602/32; 482/148; 128/845; 128/846
(58) Field of Classification Search ........... 482/140, 482/148, 49; 128/845–846; 602/32; 5/646; 606/240; 473/206; D9/434; 441/69; 16/428, 16/421; 166/241.4
See application file for complete search history.

(56) References Cited

U.S. PATENT DOCUMENTS

| | | | | |
|---|---|---|---|---|
| 2,793,917 A | * | 5/1957 | Ward | 166/241.4 |
| 2,876,486 A | * | 3/1959 | Lindstrom | 16/421 |
| 3,095,198 A | * | 6/1963 | Gasche | 473/206 |
| 3,541,990 A | * | 11/1970 | Du Mas | 441/69 |
| 4,461,287 A | | 7/1984 | Takahashi | |
| 4,753,438 A | | 6/1988 | Paris | |
| 5,437,071 A | * | 8/1995 | Feigenbaum | 5/663 |
| D367,817 S | * | 3/1996 | Halpin et al. | D9/434 |
| 5,540,643 A | | 7/1996 | Fontaine | |
| 5,575,295 A | | 11/1996 | Khalsa | |
| 5,579,551 A | * | 12/1996 | Tommaney | 5/636 |
| 5,700,053 A | * | 12/1997 | Downing | 297/227 |
| 5,722,117 A | * | 3/1998 | Nielsen | 16/428 |
| 5,947,871 A | * | 9/1999 | Gilcrease | 482/49 |
| 6,007,507 A | | 12/1999 | Ledany | |

OTHER PUBLICATIONS

Wm. T. O'Connor M. D. *Making Your Bad Back Better* © 1997 Aegis genomics Pub. ISBN 0-9664991-1-5.
Neal R. Hurd "Belly Beam" or "8th Wonder of the World" Dec. 13, 2000.

* cited by examiner

*Primary Examiner*—Lori Amerson

(57) ABSTRACT

The present invention relates to a portable spinal adjustment apparatus and method for assisting a user thereof to adjust the user's spine. The apparatus includes an elongate member which defines a substantially convex substantially rigid surface which is disposed between a first end and a second end of the elongate member. The convex rigid surface features a radius of about 2 to 4 inches, thereby defining a first side and a second side, and a length suitable to cooperate with and transversely support a body region of the user. The first end of the elongate member supports the elongate member during use thereof such that the convex rigid surface is facing upward, and the second end of the elongate member also supports the elongate member during use thereof such that the convex rigid surface is horizontal. So disposed and defined by the present invention, the convex rigid surface manifests an arcuate fulcrum, whereby employment thereof combined with the effect of gravity and simple leverage, the user is assisted in adjusting the user's spine.

12 Claims, 18 Drawing Sheets

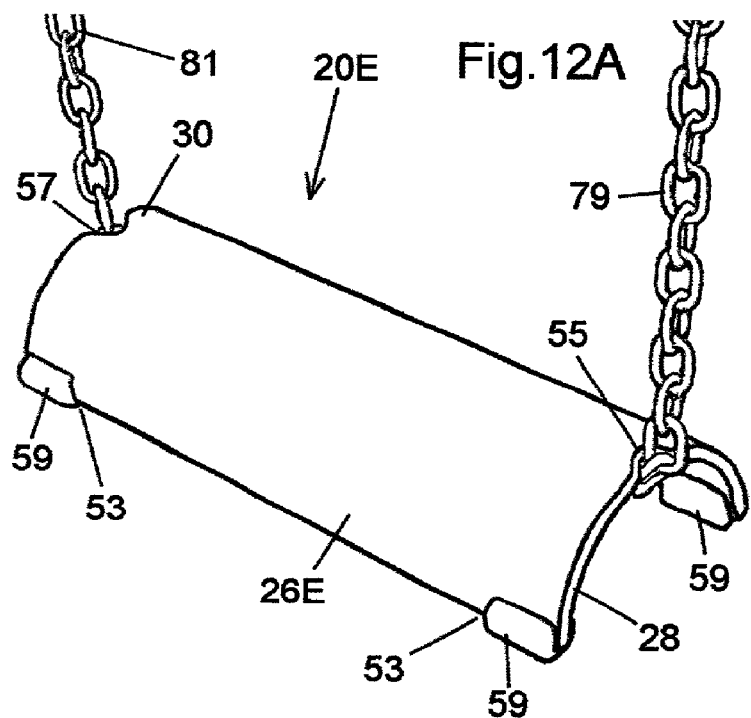
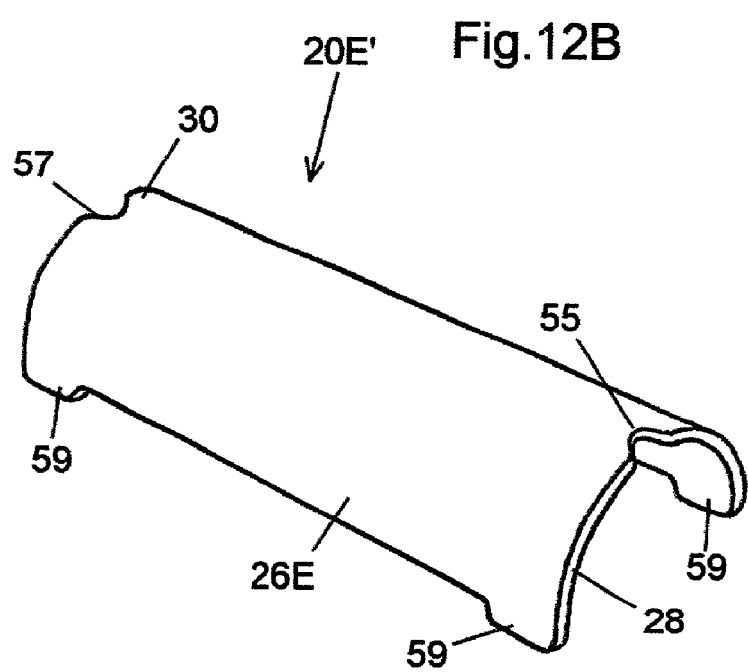

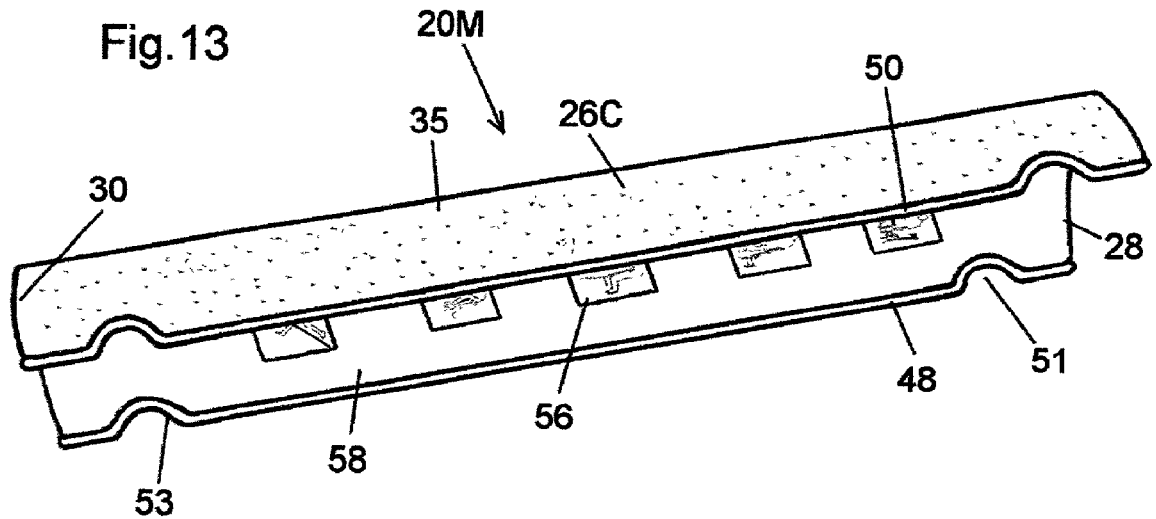

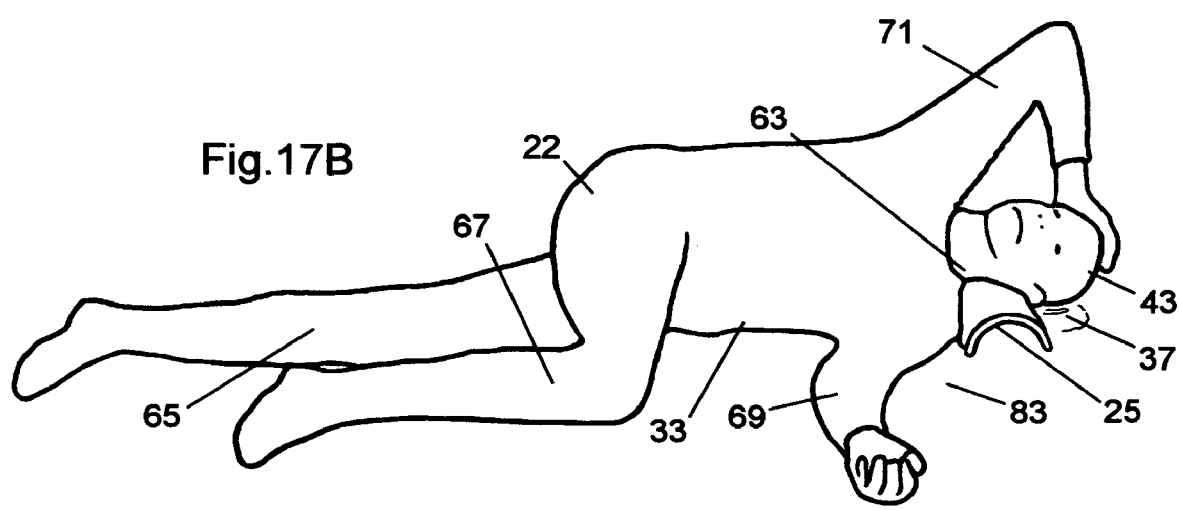

METHOD AND PORTABLE APPARATUS FOR SPINAL ADJUSTMENT

BRIEF SUMMARY OF THE INVENTION

The present invention relates to a portable spinal adjustment apparatus and method for assisting a user thereof to adjust the user's spine. The apparatus includes an elongate member which defines a substantially convex substantially rigid surface which is disposed between a first end and a second end of the elongate member. The convex rigid surface features a radius of about 2 to 4 inches, thereby defining a first side and a second side, and a length suitable to cooperate with and transversely support a body region of the user. The first end of the elongate member supports the elongate member during use thereof such that the convex rigid surface is facing upward, and the second end of the elongate member also supports the elongate member during use thereof such that the convex rigid surface is horizontal. So disposed and defined by the present invention, the convex rigid surface manifests an arcuate fulcrum, whereby employment thereof combined with the effect of gravity and simple leverage, the user is assisted in adjusting the user's spine.

The apparatus is arranged such that in one manner of use, the elongate member transversely supports an abdominal region of a user so that, under the influence of gravity acting on an unsupported lower body region of the user located distally on the first side the elongate member, and under the influence of gravity acting on an unsupported upper body region of the user located distally on the second side of the elongate member, the arcuate fulcrum provides extensively reducing resistance and path toward each side of the elongate member such that adjacent vertebrae of the user's spine are directed radially and extensively along the abdominal region of the user so divergently supported, thus relieving pressure on adjacent spinal discs. The apparatus is arranged such that in a different manner of use, inwhich the majority body region of the user is basically fully supported in either a supine or a related lateral position on the first side of the elongate member, the elongate member transversely supports either a dorsal or a lateral neck region of the user so that, under the influence of gravity acting on an unsupported head region of the user located distally on the second side of the elongate member, the arcuate fulcrum provides extensively reducing resistance and path to the second side such that adjacent vertebra of the user's spine are directed radially and extensively along the neck region so divergently supported, thus relieving pressure on adjacent spinal discs.

It is necessary to realize that the portable apparatus and method of the present invention looks to independent items for in some cases, embodiment, and in all cases support of the elongated member for deployment according to the present invention. Such support may include, for purposes of lumbar adjustment, chairs, stools, saw horses and chain, and for purposes of cervical adjustment, essentially a floor. In any case, the user determines, based on the features incorporated into the apparatus and alternative modes of practice of the method of the present invention, the most suitable arrangement.

In a generic embodiment of the present invention, suitable for lumbar spinal adjustment, the elongate member is comprised of two suitable kitchen-type chairs and paddings. In a generic embodiment of the present invention suited for cervical spinal adjustment, the elongate member is any appropriate convex item, suitably deployed.

In a manufactured embodiment of the present invention, the elongate member is fabricated from a plastics material. Alternatively, the elongate member is fabricated from fiberglass or sheet metal or from wood.

Also, in one embodiment of the present invention, the elongate member is of tubular configuration whereas, in another embodiment of the present invention, the elongate member is of inverted U-shaped/semi-circular configuration.

In a manufacture of one such embodiment of the present invention, a tube is cut axially to form two semi-circular elongate members in order to reduce costs of the apparatus.

The semi-circular and inverted U-shaped elongate members each defines a first elongate edge and a second elongate edge. In one such embodiment, a first edge padding and a second edge padding are secured respectively to the first and second elongate edges. Such edge padding can serve both to protect and adhere to the independent support during use of the apparatus. In a manufacture of the elongate member, such edge padding may be accomplished by placement of a deformable plastic at the edge during molding.

In a further embodiment, the first elongate edge defines a boost and the second elongate edge defines a boost located near each first and second end of the elongate member. The boost serves, depending on the deployment mode and the embodiment, to configure the elongate member for the proper working height or as an elevation adjustment feature for the apparatus, or based the contour it offers in opposition to independent support, as a stop feature, necessary to engage or fixate without attachment to some types of independent support for safe and secure deployment.

In a further embodiment, the first elongate edge defines a circular indentation and the second elongate edge defines a circular indentation located near each first and second end of the elongate member. The indentation serves, depending on the deployment mode and the embodiment, as the elevation adjustment feature, or as the stop feature.

Regarding the above mentioned boosts and indentations, one skilled in the art will appreciate that based on their effect as stop features with respect to independent support, "elongate member contour offering opposition" is a broad phrase for encapsulating the physical feature and effect.

In another embodiment of the present invention, the first end of the semi-circular elongate member exhibits a circular indentation at the crest of the convex surface and the second end of the semi-circular elongate member exhibits a circular indentation at the crest of the convex surface. Such crest indentation provides the stop feature for a variation of deployment.

Furthermore, the apparatus includes, in one embodiment of the present invention, indicia printed on an inside surface of the elongate member. The indicia is instructions to the user of the apparatus. More particularly, the indicia includes pictographs or diagrams, recognizable throughout the world, and connected in sequence as to how the apparatus is to be used and further pictographs showing how the apparatus is not to be used. Colors, such as for example, red or green may be associated with these pictograms.

Furthermore, in one embodiment of the present invention, the elongate member is finished with a resilient covering. In another embodiment, the elongate member is coarse textured.

In a further embodiment of the present invention, the apparatus includes a beam of rectangular cross sectional configuration, such that the beam defines a first and second flat and a first and second border. The beam extends along and is rigidly secured to the inside surface of the semi circular elongate member, the first border of the beam secured near the first edge of the elongate member and the second border of the beam secured near the second edge of the elongate member, the beam having a first and second extremity. The arrangement is such that the first extremity of the beam projects away from the first end of the elongate member and the second extremity of the beam projects away from the second end of the elongate member.

The apparatus further features the resilient covering which encloses the elongate member and is attached to the beam at the available flat thereof. Such covering can serve to finish the apparatus as well as increase comfort in use of the apparatus and in this embodiment provides the stop feature as well.

In addition, the apparatus includes a first non-slip pad which is secured to the first extremity of the beam, adjacent to the stop, so that in use of the apparatus, when the beam is on support at the first extremity, the first non-slip pad inhibits lateral slippage of the first extremity. A second non-slip pad is likewise secured to the second extremity of the beam so that in use of the apparatus, when the beam is on support at the second extremity, the second non-slip pad inhibits lateral slippage of the second extremity.

In another embodiment inwhich the beam is incorporated, the elongate member is of the tubular configuration.

Additionally, in one such embodiment, the first extremity of the beam defines a first hole and a support extends through the first hole and is anchored to the first extremity for supporting the first extremity. Moreover, the second extremity of the beam defines a second hole and a further support extends through the second hole and is anchored to the second extremity for supporting the second extremity. More specifically, the support and the further support are a first and a second chain respectively. Those skilled in the art will appreciate that rope or strap could be used in place of the chains.

Additionally, the first and second hole can be fairly large so that when the backs of curved chairs are used to support the device, diametrically opposite sides of each of the holes will engage the curved back of a respective chair so as to avoid any rocking action of the device relative to the chairs. Additionally, the first non-slip pad, in use of the apparatus, is supported upon a chair and the second non-slip pad is supported upon a further chair.

In a further embodiment, the beam is secured to the tubular member such that each flat of the beam defines a distinct chord which extends internally within and across the elongate tubular member. The arrangement is such that when the beam is supported on the first flat, the tubular member is disposed in a first location thereof and when the beam is supported on the second flat, the tubular member is disposed in a second location thereof, the second location being a different elevation than the first location.

The method of spinal adjustment of the present invention is most easily discussed in light of the drawing figures.

Many modifications and variations of the present invention will be readily apparent to those skilled in the art by a consideration of the detailed description contained hereinafter taken in conjunction with the annexed drawings which show a preferred embodiment of the present invention. For example, as an alternative to the rectangular beam, a tubular elongate member could have projections provided by molding or by removal of material at each extremity to provide for engaging independent support. As another example, a portable apparatus that provides lumbar adjustment in the manner of the present invention could include attendant co-designed support to substitute for independent support. Furthermore, features included in the various embodiments of the present invention could be removed whereby the application of the invention would be narrowed without the functionality being lost. However, such modifications and variations fall within the spirit and scope of the present invention as defined by the appended claims.

BRIEF DESCRIPTION OF THE SEVERAL VIEWS OF DRAWING

FIG. 12A is a perspective view of a reduced embodiment of the apparatus;

FIG. 12B shows a manufacturing modification of the apparatus of FIG. 12A;

FIG. 13 shows another embodiment with indicia on the inside surface;

FIG. 17B is a full length view of the adjustment of FIG. 17A from a different angle;

Similar reference characters refer to similar parts throughout the various embodiments of the present invention.

DETAILED DESCRIPTION OF THE INVENTION

Figure 1:
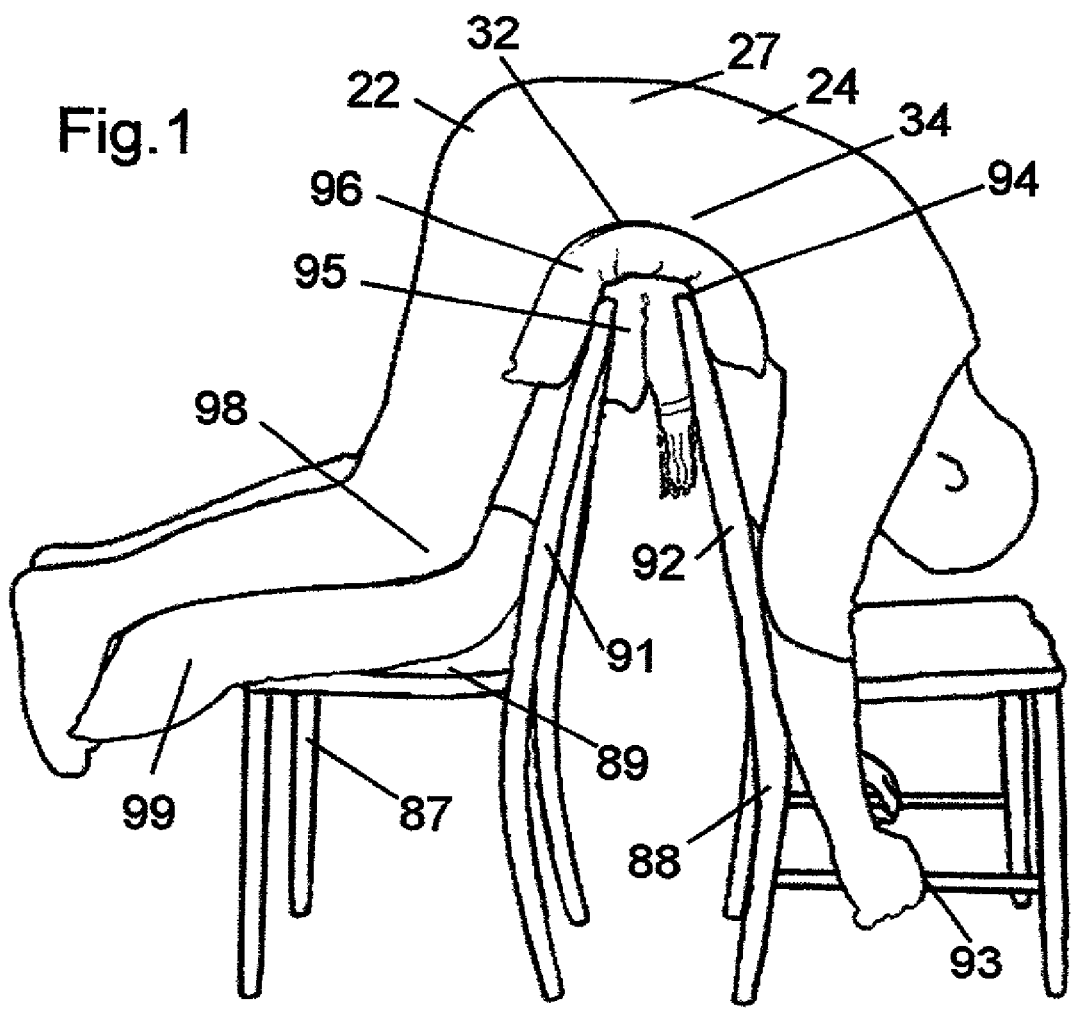
FIG. 1 is a side elevational view of a generic embodiment and the method of spinal adjustment of the lumbar vertebrae according to the present invention.

FIG. 1 is a side elevational view of a generic embodiment and lumbar 27 spinal adjustment according to the present invention. As shown in FIG. 1, a user 22 employs items commonly found in a home to adjust the user's spine 24. In this case, separation padding 95 is folded and sandwiched between chair backs 91 and 92 of chairs 87 and 88 respectively, such that it extends above and covers top(s) 94 of the chair backs. A shape padding 96 is used to combine with the separation padding 95 and chair backs 91 and 92 to provide a substantially convex elongate horizontal surface 32 with a compressed diameter of about 6 to 8 inches to address the user's abdomen 34. A knee 98 padding 99 is positioned on chair seat 89. The user has a control factor 93.

Figure 2:
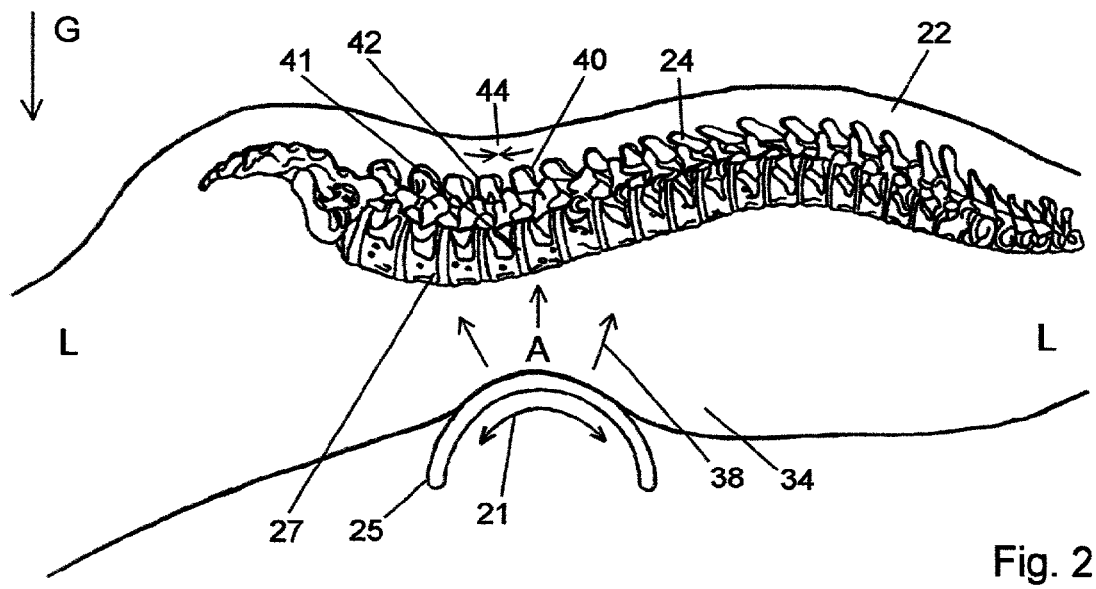
FIG. 2 is a schematic view of an apparatus and it's action in relationship to the lumbar spinal column.

FIG. 2 is a schematic view of an apparatus and the it's action in relationship to the lumbar spinal column. Gravity G, leverage L and arch A are combined to adjust the spine 24. A user 22 transversely supports an abdominal region 34 on arcuate fulcrum 25, which defines a substantially convex substantially rigid surface with a radius of about 2 to 4 inches and a length suitable to transversely support a body region of the user. The arcuate fulcrum 25, being fully disposed against the flow of gravity G equally along it's length, provides extensively reducing resistance and path 21 to the unsupported body weight of the user at L and L whereby opposition pressure 38, provided by arch A, acting on adjacent vertebrae, is leveraged to effect decompressive adjustment to misaligned lumbar 27 vertebrae 40 and 42 whereby pressure 44 on disc 41 is reduced.

Figure 3:
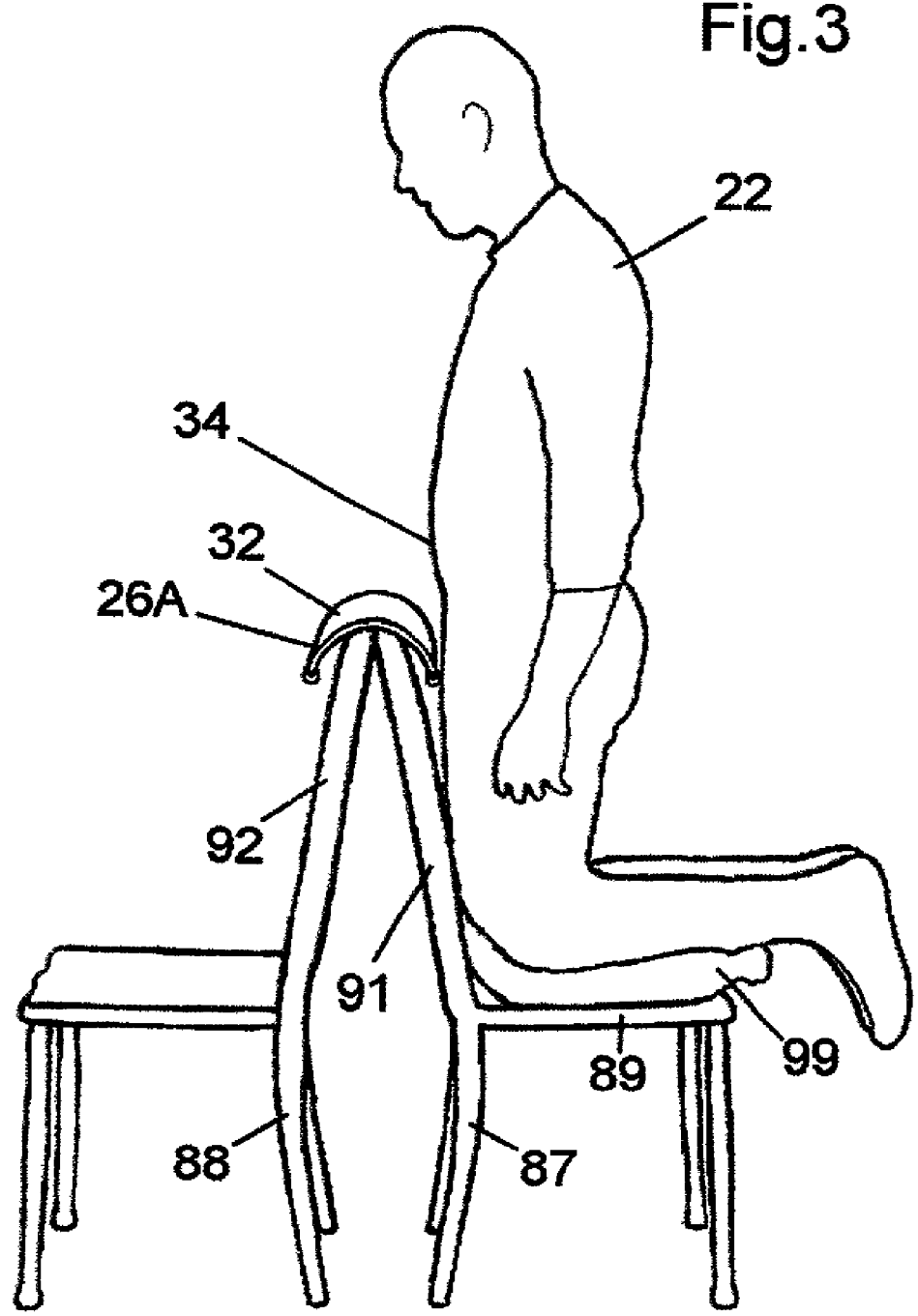
FIG. 3 is a view similar to FIG. 1 but with a manufactured apparatus of the present invention in position for use.

FIG. 3 is a view similar to FIG. 1 but with a manufactured apparatus of the present invention in position for use. Chair backs 91 and 92 of chairs 87 and 88 respectively provide support for semi circular elongate member 26A placed longitudinally thereon whereby user 22 kneeling on knee padding 99 placed on chair seat 89 can support abdomen 34 on horizontal convex surface 32 to adjust the spine.

Figure 4:
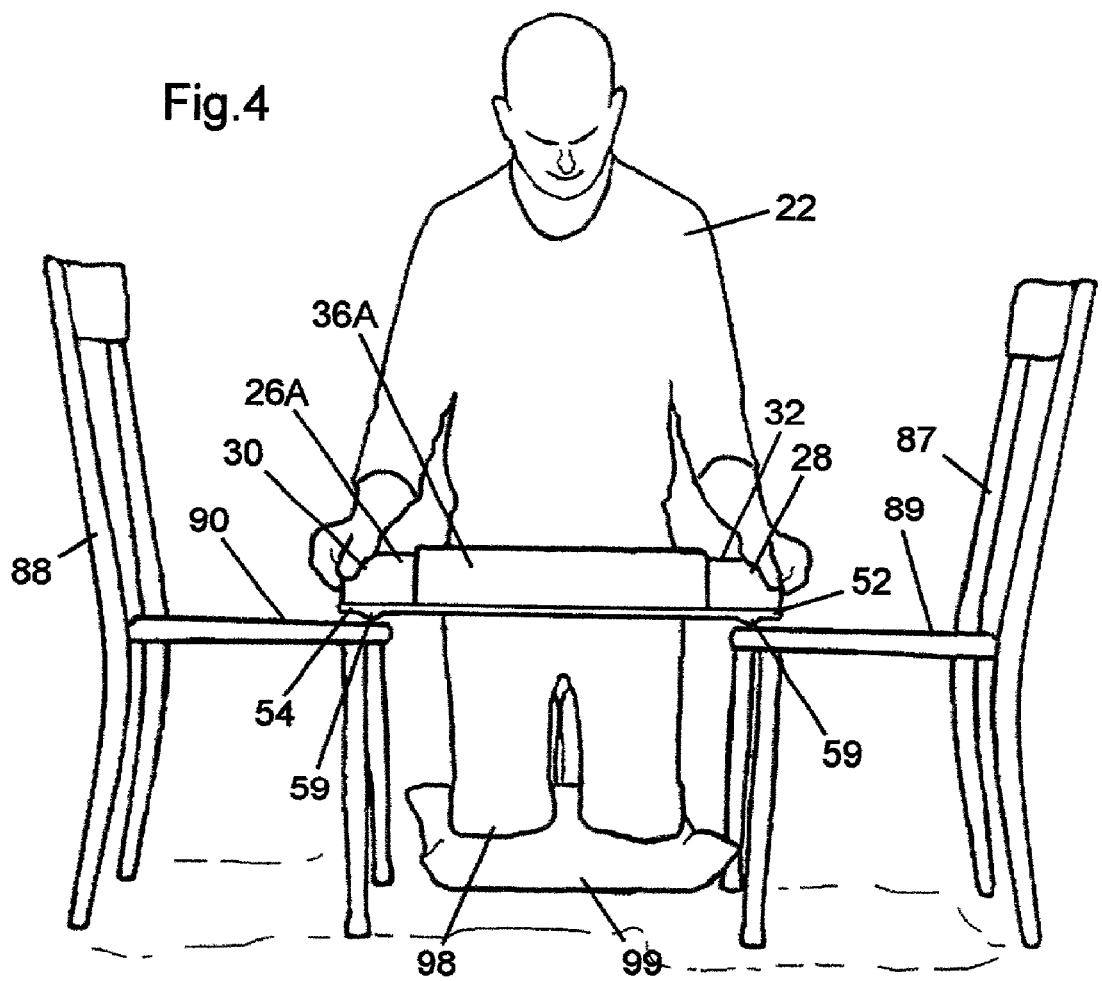
FIG. 4 is a view of the elongate member deployed for use in another fashion according to the present invention.

FIG. 4 is a view of an apparatus deployed for use in a variation of deployment according to the present invention. The elongate member 26A has a first and a second end 28 and 30 respectively. The elongate member 26A defines a rigid convex surface 32 which is disposed between the first and second ends 28 and 30 respectively, with a resilient cover, 36A attached. With a first and second edge padding, 52 and 54 respectively and associated boosts 59 positioned on first and second chairs 87 and 88 respectively seats 89 and 90, the elongate member 26A is positioned for user 22, kneeling 98 on knee padding 99 to adjust the lumbar spine. The first end 28 of the elongate member 26A supports the elongate member during use thereof such that the convex surface 32 faces upward against the flow of gravity. The second end 30 of the elongate member 26A also supports the elongate member during use thereof such that the elongate member is disposed substantially horizontal so that in use of the apparatus, the user 22 supports the abdominal region of the user in contact with the resilient covering 36A so that the rigid surface 32 exerts a spine adjusting opposition pressure, through the abdominal region of the user.

Figure 5:
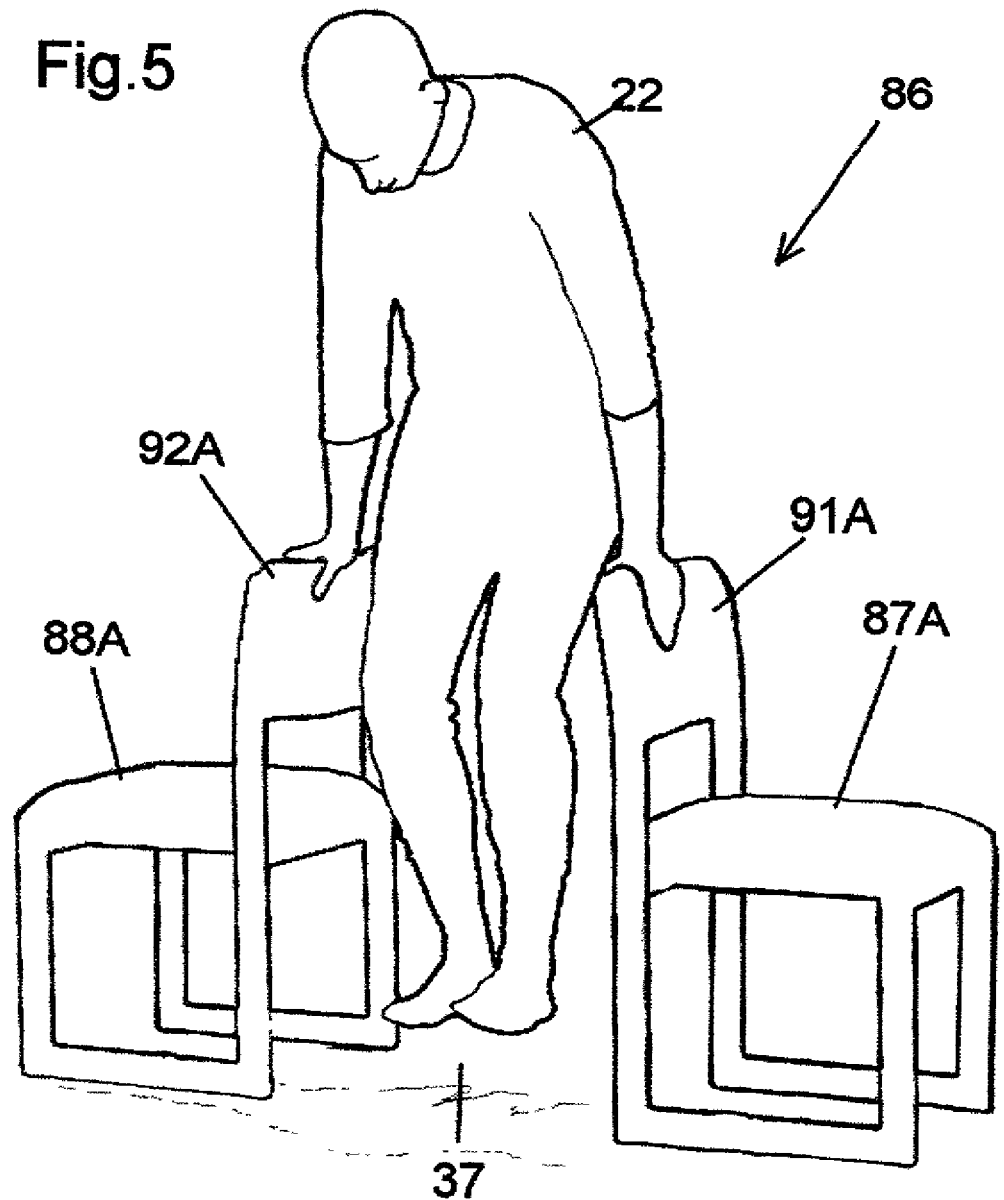
FIG. 5 is a view of a necessary step for a variation of deployment of the apparatus of the present invention.

FIG. 5 is a view of a necessary step for a variation of deployment of the apparatus of the present invention. User 22 positions chairs 87A and 88A with back 91A to back 92A about shoulder width apart, and with a hand on top of each back 91A and 92A, user supports whole body weight on chair backs 91A and 92A with feet gapped 37 off support, thus testing 86 chairs 87A and 88A for suitable sturdiness for a variation of deployment of the apparatus of the present invention.

Figure 6:
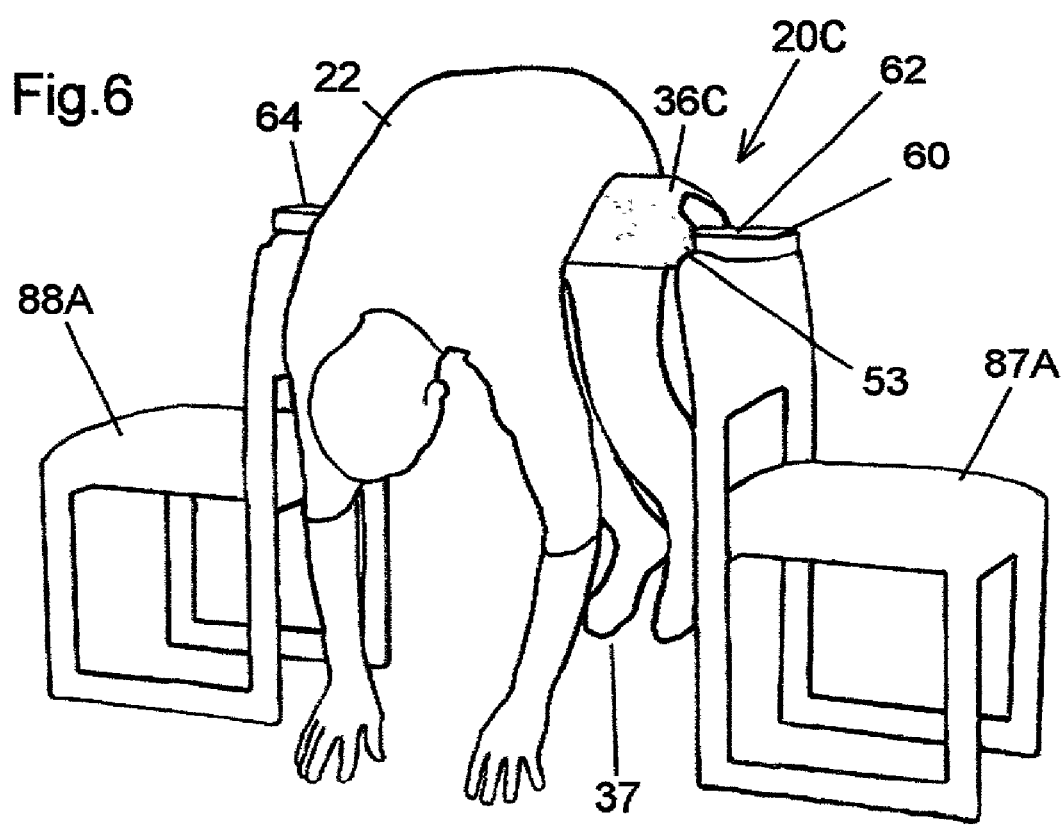
FIG. 6 is a perspective view of one mode of practice of the method and apparatus according to the present invention.

FIG. 6 is a perspective view of one mode of practice of the method for lumbar adjustment and apparatus according to the present invention. First chair 87A supports a first extremity 62 of a beam 60 of apparatus 20C, which has resilient cover 36C attached, and second chair 88A supports a second extremity 64 of beam 60 with stop 53 engaging the back of chair 87A. See FIG. 9. Based on the elevation of the apparatus, user's 22 feet are gapped 37 off support.

Figure 7:
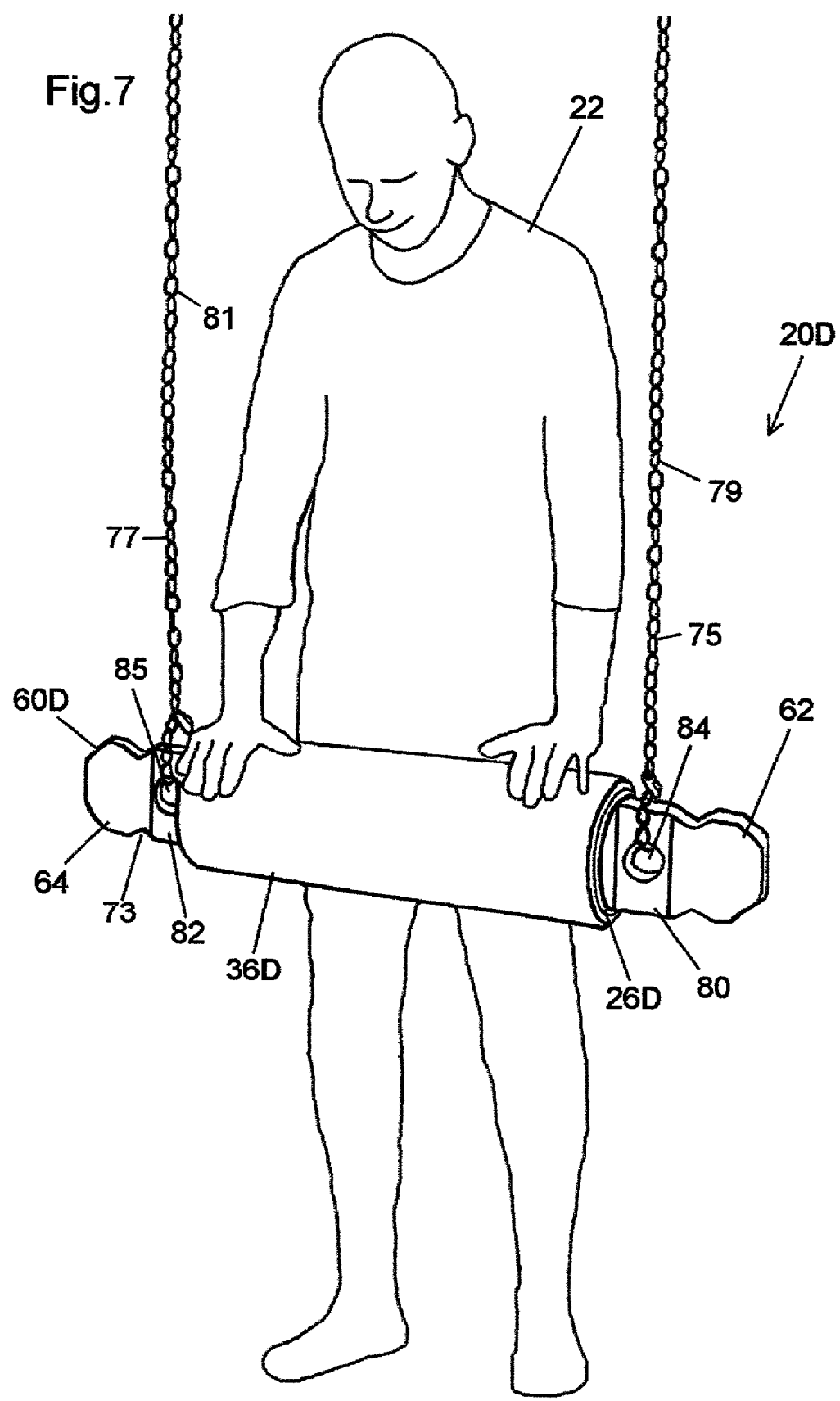
FIG. 7 is a view of a different embodiment and variation of deployment.

FIG. 7 is a view of a different embodiment and variation of deployment. User 22 has deployed apparatus 20D on a first and a second support 75 and 77 respectively in the form of a first and second chain 79 and 81 respectively so that the apparatus is positioned at approximate waist level of the user, based on the adjustability of the chains 79 and 81. The first support passes through a first hole 84 in first extremity 62 of beam 60D and the second support passes through a second hole 85 in second extremity 64 of beam 60D. Beam 60D is also characterized by notch(s) 73 to accept support 75 and 77 in a variation of this deployment inwhich the chain would simply encircle the beam at the notches. A first and a second non-slip padding 80 and 82 respectively are provided to contact solid support in a variation of deployment. Elongate member 26D is of tubular configuration through which beam 60D passes and is joined thereto and has resilient cover 36D attached. Additionally, the first and second hole, 84 and 85 respectively, are fairly large so that when the backs of curved chairs are used to support the device in a variation of deployment, diametrically opposite sides of each of the holes will engage the curved back of a respective chair so as to avoid any rocking action of the device relative to the chairs.

Figure 8:
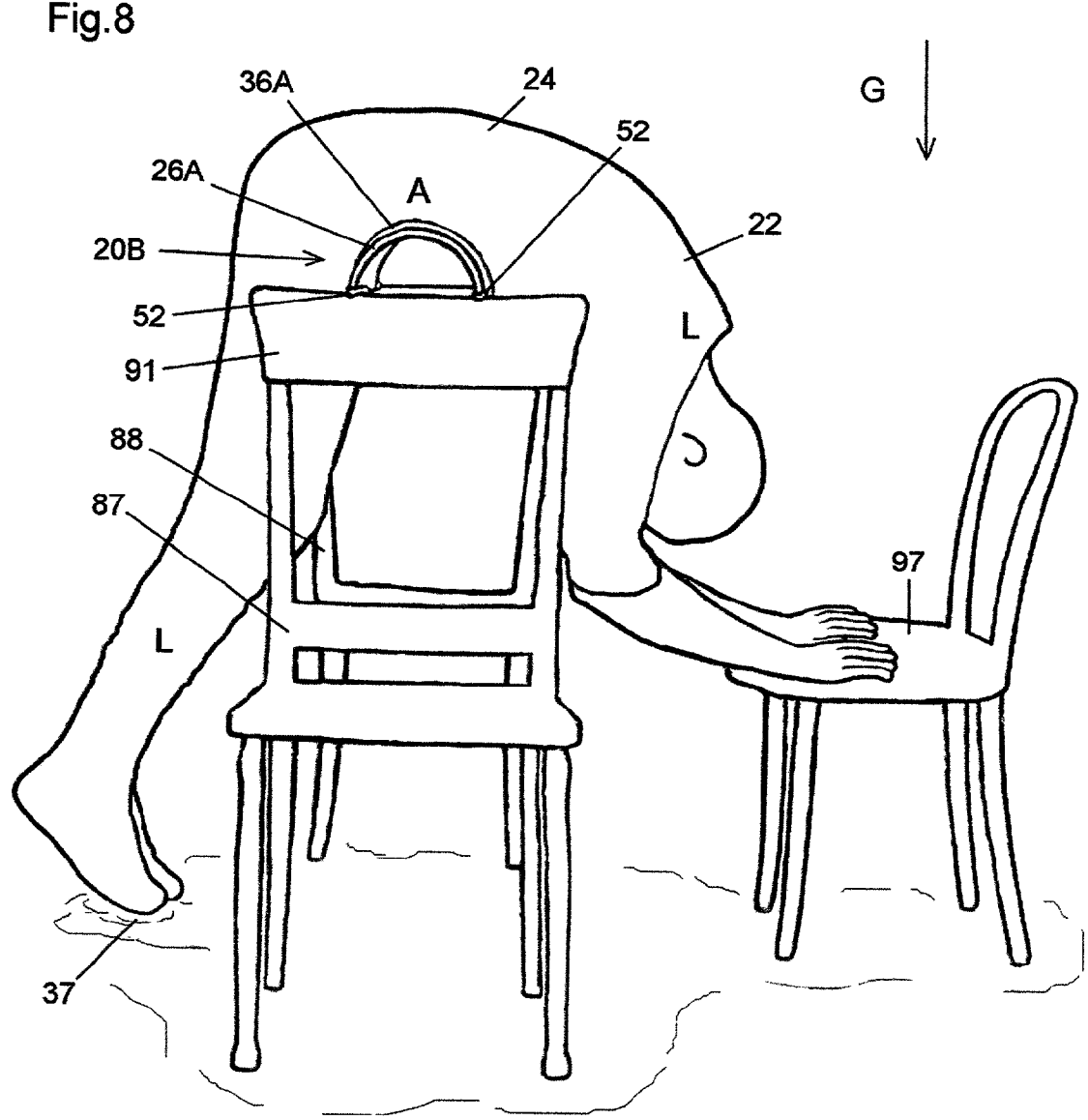
FIG. 8 is view of a user adjusting the user's spinal column with an embodiment of the invention.

FIG. 8 is view of a user 22 adjusting the user's spinal column 24 with an embodiment 20B of the invention. First chair 87 and second chair 88 support apparatus 20B at their center, with first edge pad(s) 52 in contact with back 91 of chair 87. G, L & A have combined to effect adjustment from FIG. 2 with the user unsupported at gap 37 and in passive contact with piece 97 for control. Resilient cover 36A is shown, attached to elongate member 26A.

Figure 9:
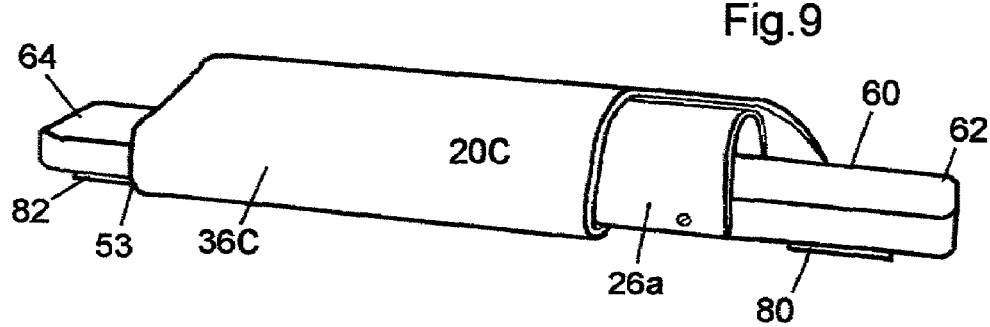
FIG. 9 is a cut-a-way view of the embodiment of FIG. 6.

FIG. 9 is a cut-a-way view of the embodiment of FIG. 6. Elongate member 26A is attached to beam 60 which has a first and a second non-slip padding 80 and 82 attached to a first and second extremity, 62 and 64 respectively. Resilient cover 36C extends around the edge to the securable flat of beam 60 thus defining stop 53.

Figure 10:
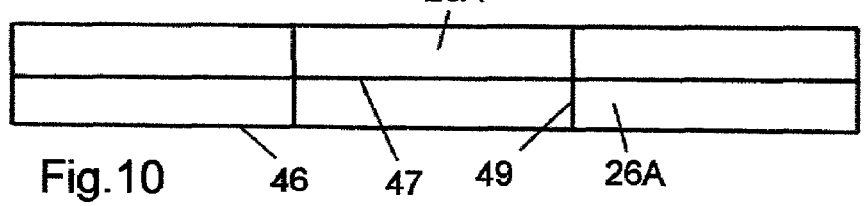
FIG. 10 is a side elevational view of a tube for manufacturing several elongate members according to the present invention.
Figure 10A:
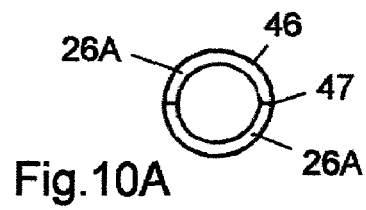
FIG. 10A is an end view of FIG. 10.

FIG. 10 is a side elevational view of a tube for manufacturing several elongate members according to the present invention. As shown in FIG. 10A, during a manufacture of the elongate member 26A, a tube 46 is cut axially as indicated at 47 and transversely at 49 to form two semi-circular elongate members 26A in order to reduce manufacturing costs of the apparatus.

FIG. 10A is an end view of FIG. 10. As shown in FIG. 10A, the tube 46 is cut at 47 to form elongate members 26A from both halves.

Figure 11:
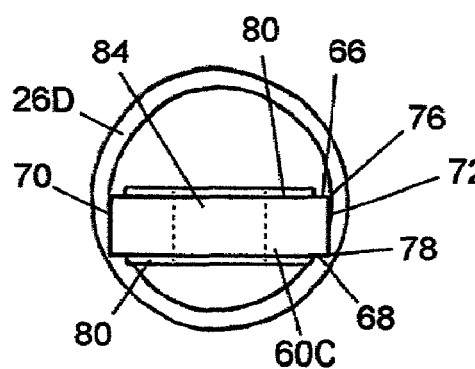
FIG. 11 is an end view of a variation of the tubular apparatus of FIG. 7.

FIG. 11 is an end view of a variation of the tubular apparatus of FIG. 7. As shown, the end view configuration of the beam 60C defines a first and a second flat 66 and 68 respectively and a first and a second border 70 and 72 respectively so that the first flat 66 of the beam 60C defines a chord 76 which extends internally within and across the elongate tubular member 26D. The arrangement is such that when the beam 60C is supported on a solid support on the first flat 66 of the beam 60C, the tubular member 26D is disposed in a first location 76, whereas when beam 60C is supported on a solid surface on the second flat 68, which is slightly cambered along that portion passing through tubular member 26D for fit engagement of the inside surface, the tubular member 26D is disposed in a second location 78, the second location being higher than the first. First non-slip pad(s) 80 are provided to contact solid support and first hole 84 is available for engaging support in a variation of deployment.

Figure 16A:
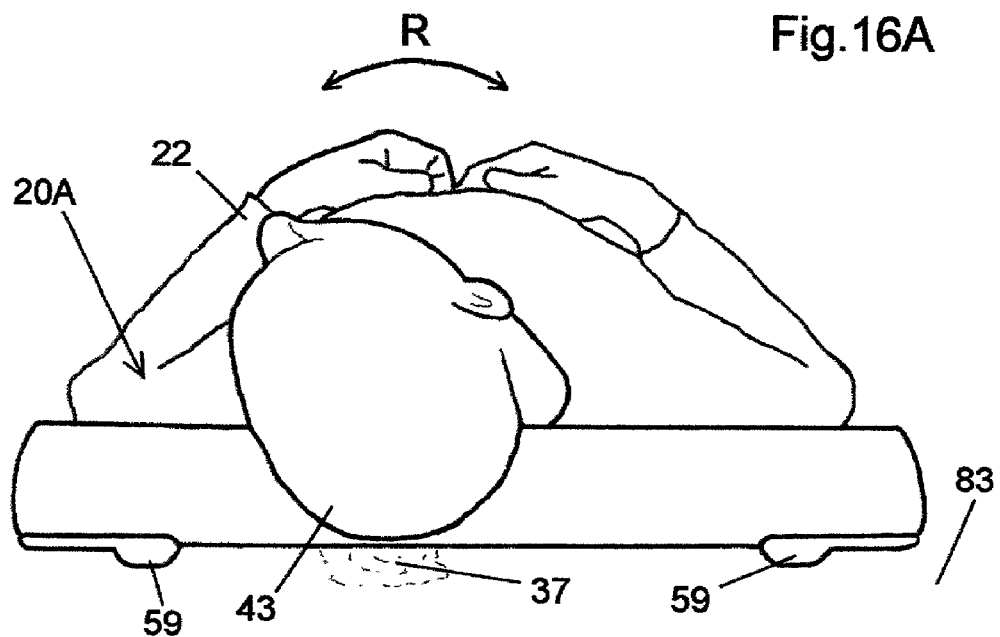
FIG. 16A is a view of an apparatus and method of use for cervical spine adjustment according to the present invention.

FIG. 12A is a perspective view of a reduced embodiment of the apparatus. The convex rigid surface, as defined by elongate member 26E, features a length, in this case about 15 inches, suitable to cooperate with and transversely support a body region of a user, and provides a first crest indentation 55 and a second crest indentation 57 communicating with a first end 28 and a second end 30 respectively at the crest of the convex surface for accepting and stopping a respective working portion 79 and 81 of support chain, in this case 3/16 inch proof coil, which is continuous beneath 26E. Boosts 59 are provided to elevate the apparatus for use of cervical adjustment for maintaining gap 37 as seen in FIG. 16A. In view 12A, they are fashioned of longitudinally slit-one-side rubber tubing, securely attached.

It should be noted that as an alternative to the support technique shown, that each chain 79 and 81 could define a loop in itself and encircle it's respective end 28 and 30, thus each chain supporting elongate member 26E in contact with the first and second elongate edges, and stopped 53 by boosts 59.

FIG. 12B shows a slight modification of the apparatus of FIG. 12A. In a manufacture of the apparatus 20E' boosts 59 could be included as shown, which would give the elongate member a somewhat inverted U-shape end view profile. It is understood that the apparatus 20E' and 20E of FIG. 12A are not designed, based on their abbreviated length for deployment as in, for example, FIG. 6 but would well serve as in FIG. 3. As shown, 20E' provides a first circular crest indentation 55 and a second circular crest indentation 57 communicating with a first end 28 and a second end 30 respectively at the crest of the convex surface for accepting a respective working portion of support chain or rope, for purposes of lumbar adjustment via deployment similar to FIG. 7 and FIG. 12A.

FIG. 13 shows another embodiment with indicia 56 on an inside surface 58. Apparatus 20M further defines circular indentations 51 which serve as stops 53 communicating with a first and a second edge 48 and 50 respectively in proximity of first and second ends 28 and 30. In this embodiment, during a manufacture, elongate member 26C is textured 35 and edges 48 and 50 have incorporated deformable plastic to serve as edge padding to adhere to and protect independent support. The length of elongate member 26C is about 26 inches.

Figure 14:
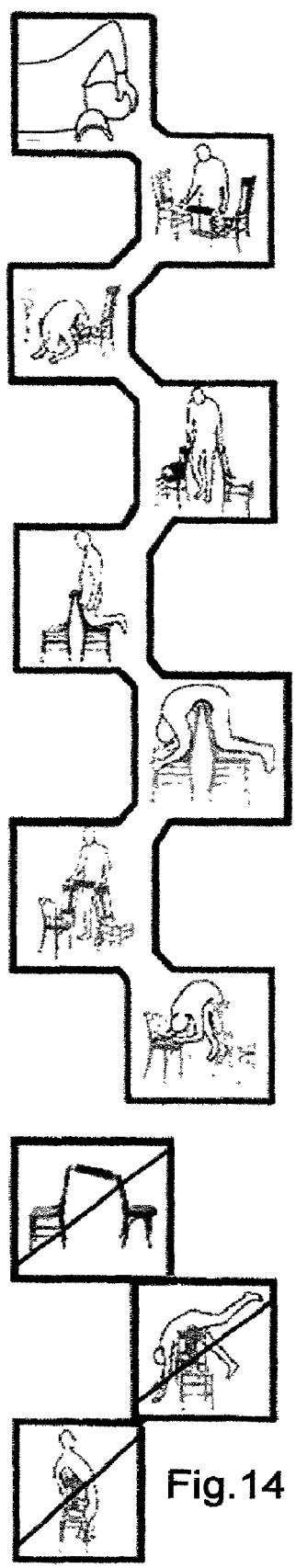
FIG. 14 is a representation of the indicia as they would appear on the apparatus.

FIG. 14 is a representation of indicia as they may appear on an apparatus. The indicia is instructions for a user of the apparatus. More particularly, the indicia includes pictographs or diagrams, recognizable throughout the world and connected in sequence as to how the apparatus is to be used and further pictographs showing how the apparatus is not to be used. Colors, such as red or green, may be associated with the inditia.

Figure 15A:
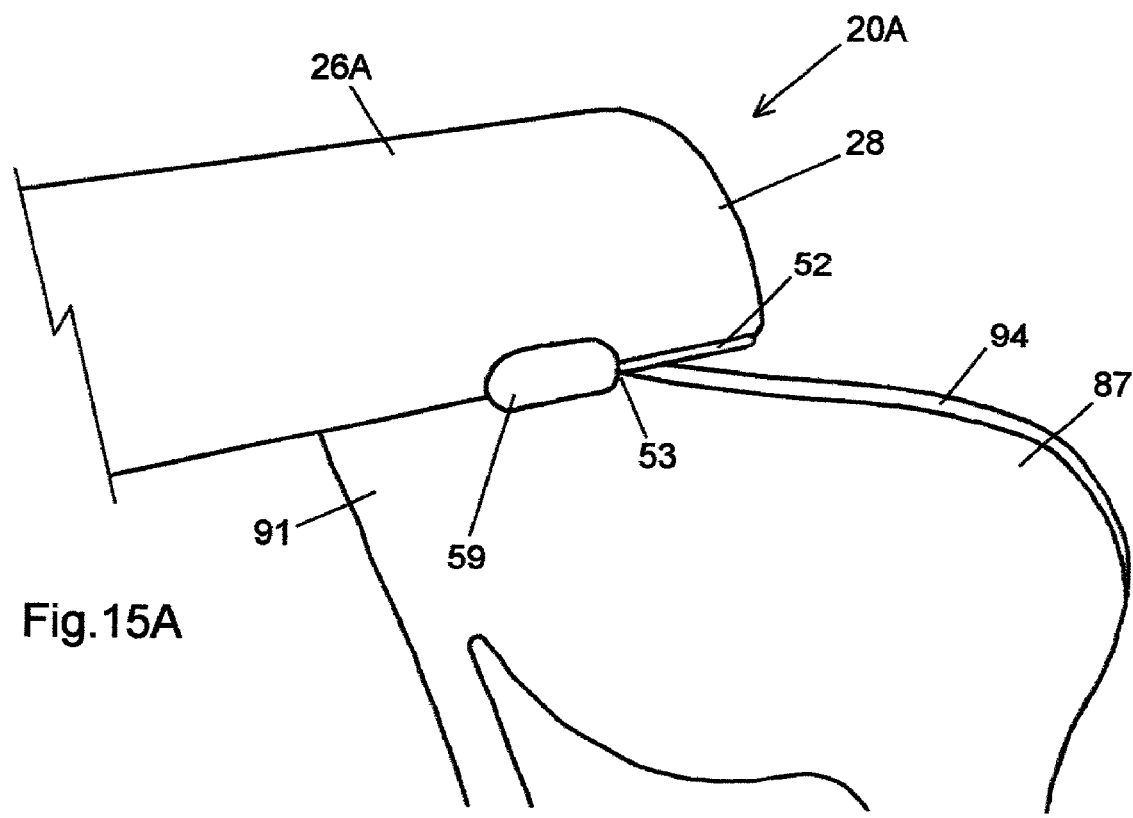
FIG. 15A is a partial view of the apparatus in position for use.

FIG. 15A is a partial view of apparatus 20A in position for use. First end 28 edge pad 52 of elongate member 26A, is communicating with top 94 of first chair back 91 to prevent lateral slippage of the apparatus. In addition, boost 59 is communicating with chair back 91 such that it prevents first chair 87 from tipping backward, thereby providing stop 53. The stop feature here detailed is essential to secure deployment of the apparatus as shown, to retain the chair from tipping backward toward the user. See FIG. 6 and FIG. 8. In alternative deployment depending on a chain loop encircling 26A, the stop feature would be realized at the opposite end of the boost, to retain the chain from slipping off the end of 26A.

Figure 15B:
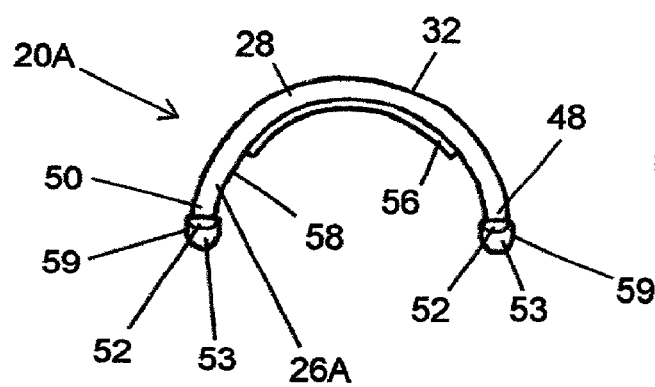
FIG. 15B is an end view of the apparatus of FIG. 15A.

FIG. 15B is an end view of the apparatus of FIG. 15A. As shown, the semi-circular elongate member 26A defines a first and a second elongate edge 48 and 50 respectively. Also, a first end 28 edge padding 52 are secured to the first and second elongate edges 48 and 50 respectively for providing a non-slip feature to the elongate member 26A. In addition, boosts 59 provide stops 53, necessary for deployment as shown in FIG. 15A. Furthermore, the apparatus 20A includes in one embodiment of the present invention, indicia 56 printed on an inside surface 58 of the tubular member 26A. In regard to convex dimensions, for purposes of lumbar adjustment according to the present invention, a radius of about 3 to 4 inches is suitable for all but the largest of user's, whereas for purposes of cervical adjustment according to the present invention, a radius of about 3 inches is proper. Hence, for an apparatus to be effective for both, a working surface radius of about 3 inches is best. A user can adjust this up with covering material for lumbar adjustment.

FIG. 16A is a view of an apparatus and method of use for cervical adjustment according to the present invention, specifically C.A. mode 1. User 22 is supine on a horizontal plane substantially rigid support surface 83 with apparatus 20A, also supported on surface 83, disposed transversely beneath the user's neck with boost(s) 59 providing elevation to apparatus 20A so that the user's head 43 is unsupported at gap 37. So disposed, the user is at liberty to direct an amount of appropriate slow back and forth rotation R to the head 43 to effect a cervical spine adjustment.

Figure 16B:
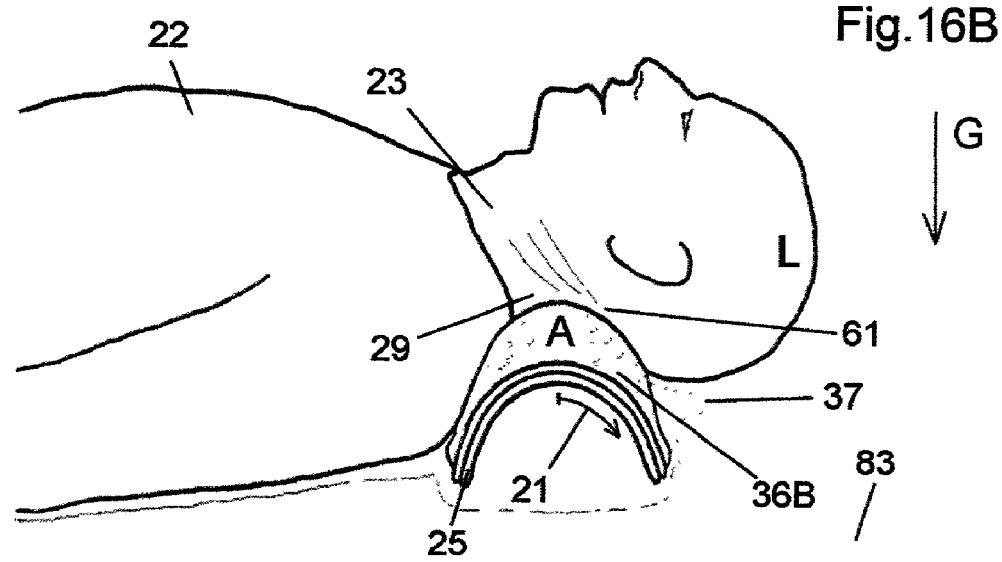
FIG. 16B is a side view of cervical adjustment according to the present invention.

FIG. 16B is a side view of cervical adjustment according to the present invention. User 22 is positioned to effect cervical spine 29 adjustment utilizing G, gravity L, leverage and A arch. The user is supine on a horizontal plane substantially rigid support surface 83 with a dorsal 61 neck 23 region transversely supported on an arcuate fulcrum 25 which is likewise supported on the surface 83 and drawn in equal and tight to the user's shoulders. Arcuate fulcrum 25, being disposed against the flow of gravity G, provides, due to gap 37 and the fully supported supine body of the user, extensively reducing resistance and path 21 to the unsupported head region at L. Opposition pressure, provided by resilient covered 36B arch A and augmented by slow back and forth rotation of the user's head, is leveraged to effect decompressive adjustment to adjacent vertebrae, whereby pressure on adjacent cervical discs is reduced.

Figure 16C:
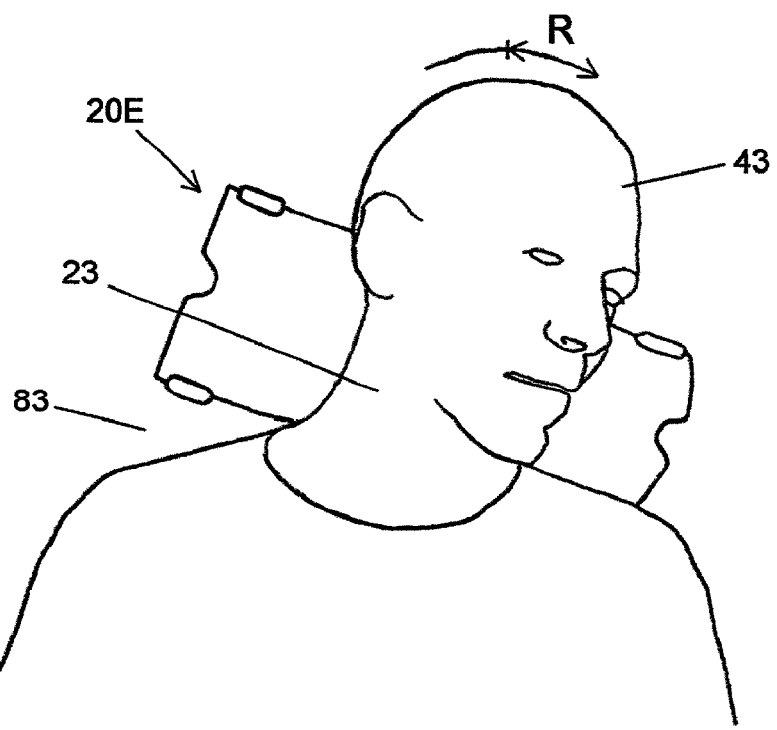
FIG. 16C is a third view and mode 2 of cervical spine adjustment using a reduced apparatus.

FIG. 16C is a third view and variation of the method of cervical adjustment as defined by the present invention, specifically C.A. mode 2. As in the previous views of cervical adjustment the apparatus and user are supported on plane surface 83. However, the apparatus, in this view 20E, which in the previous mode of adjustment of FIGS. 16A and 16B was equally tight to both shoulders of the user, is in this mode of adjustment angled to a side to facilitate a further rotation R of the head 43 toward that one side. It is understood that a similar move is necessary toward the opposite side for purposes of balanced adjustment of the neck 23. Such an adjustment can serve to increase flexibility.

Figure 17A:
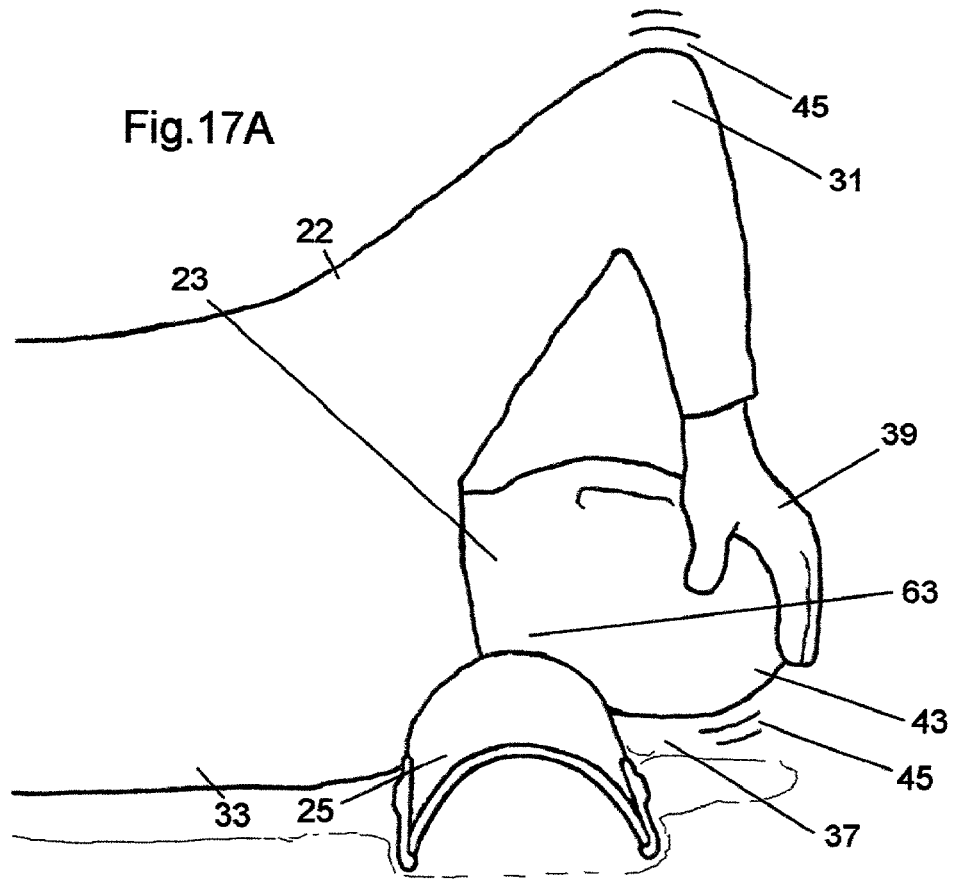
FIG. 17A is a view of a further mode 3 of adjustment of the cervical vertebrae as defined by the present invention.
Figure 18A:
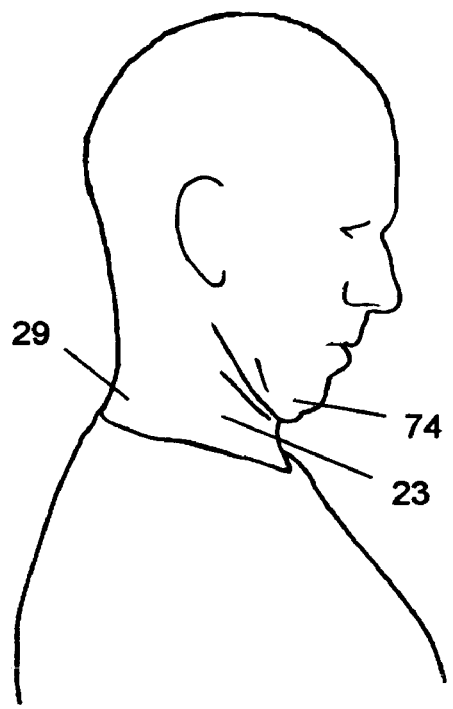
Figure 18B:
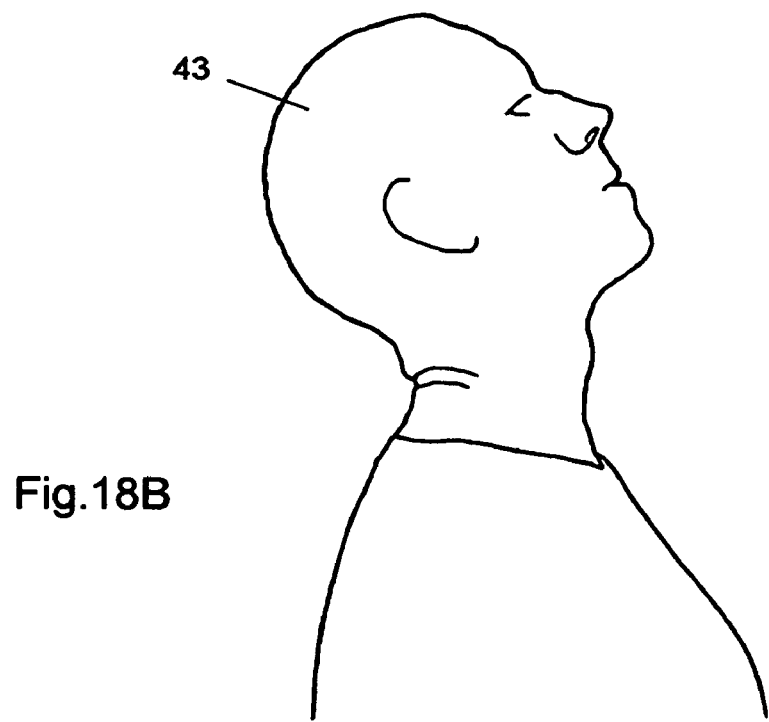
Figure 19:
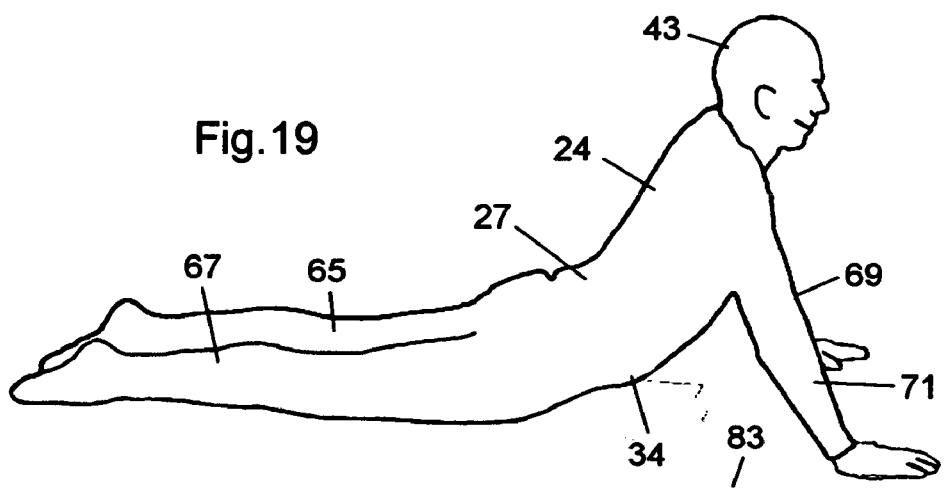

FIG. 17A is a view of a different mode of adjustment of the cervical vertebrae of the present invention, specifically C.A. mode 3. User 22 is positioned on a side 33 such that a lateral 63 region of neck 23 is supported on arcuate fulcrum 25. The user has hand 39 only resting on head 43 with elbow 31 disposed above. No pressure 45 is being applied, as the unsupported weight of the user, which in this case includes the resting weight of 31 and 39, is sufficient based on gap 37, to effect adjustment. It is understood that a similar move to the opposite side is necessary for balanced adjustment of the neck 23.

The first and most basic mode 1 and somewhat mode 2 is best for routine practice, with mode 3, being more radical, available to address kinks at the side of the neck. In such cases, the problem should be approach from the opposite side, whereby the offending kink is away from the arcuate fulcrum. Based on the combined effect of G, L, and A, the time interval of cervical adjustment according to the present invention is about 1 minute per each move of the three modes, with an at most once daily routine suitable for effecting improved cervical fitness and flexibility over a period of a few weeks. The user should be somewhat careful of abrupt moves initially, as the neck is a bit destabilized due to decompression, until the discs catch up via rehydration. Since, as is the case for the method of spinal adjustment of the present invention in general, this is a user initiated and practiced method, the user is responsible for monitoring and determining the suitability of any and all adjustments here defined. No doctors were consulted concerning the method of spinal adjustment depending on Gravity, Leverage and the Arch.

FIG. 17B is a full length view of the mode of adjustment of FIG. 17A. Positioned on side 33, the user's upper leg 67 is bent at the knee and placed on or slightly in front of the lower leg 65 so that the upper hip is at least above the lower hip. The user's lower arm 69 is extended out on support 83 with the lower shoulder somewhat ahead of the neck to facilitate supporting the lateral 63 neck region on the arcuate fulcrum 25. The upper arm 71 is only resting on the head 43, as cervical adjustment is effected based solely on the unsupported body weight of the user, which in this case includes the resting weight of arm 71, relative to gap 37. As an alternative, the user can raise the forward end of the apparatus with the lower hand to elevate the convex surface to more easily address the lateral neck. As a further alternative, the user can rotate the apparatus up onto the edge closest to the body to elevate the convex surface to more easily address the lateral neck. On the other hand, in use of the tubular apparatus FIG. 7 of the present invention for cervical adjustment, a user may need to provide lift padding to the supported body region to maintain a proper relationship to the arcuate fulcrum.

In operation of the apparatus for lumbar adjustment according to the present invention, while most prior art devices designed for relieving low back pain include means for pressing against the users back in the vicinity of the misaligned vertebrae, the present invention provides an apparatus which is applied to the user in the abdominal region of the user so that the weight of the user is occupied in a controlled way to urge the adjacent spinal vertebrae radially along the abdomen and the arch form of the apparatus so that pressure between such misaligned spinal vertebrae is reduced. This adjustment action is carried over to the skeletal members adjacent to the column structure, and, for example the pelvis is allowed to rotate into a natural alignment relative to the sacrum and hips, and the head and neck and shoulders, if properly relaxed, do similarly in their turn.

In each of the described embodiments for lumbar adjustment, after proper testing of the independent support FIG. 5 as necessary, and proper deployment of the apparatus FIG. 15A, the user carefully leans forward, moving in a primarily vertical manner, over the convex rigid surface 32 and transversely supports a region of the low to mid abdomen. The placement chosen affects the balance point and since there is a learning curve to anything new, it is always recommended to begin practice of the method from the low, seat height mode FIG. 4 or the back to back chair deployment mode FIG. 3, as the user has good control at hand in either case. Also, by proper use of knee padding 99, a lift feature can be realized to further enhance control. The user then gradually allows the user's weight to become supported by the apparatus so that if necessary, the whole of the user's weight is supported by the apparatus so that the rigid surface 32 exerts a spinal adjusting pressure 38 applied from the user's abdominal region 34 toward the misaligned vertebrae for tending to reduce the pressure between adjacent vertebrae. No effort on the part of the user is necessary or desired, as the combined and powerful effect of G L & A is all sufficient. The total time interval of lumbar adjustment so described is about 5 seconds, after which the user returns to a starting position.

That 5 second interval is about the time it takes for the adjustment effect to manifest itself from the area of maximum support, perpendicular to the arcuate fulcrum 25 toward each end of the spinal column, as the expansively reducing resistance and path 21 provided by the apparatus, combined with relaxation on the part of the user effects adjustment. It is recommended that new users consult with a health care professional, as none were referred to in the development of this method and a certain amount of pressure to the abdomen must be tolerated. A user should also always provide a control piece 93 or 97 for lumbar adjustment, and be on guard and maintain contact with the apparatus after dismounting, as dizziness can occur. A second person could be present to safely become familiar with the method. Control and safety are always in order in the deployment and practice of this powerful and effective low back adjustment.

The various embodiments provide different means for accomplishing the aforementioned adjustment. More specifically, the apparatus can be supported at the extremities thereof by chains 79 and 81 so that the apparatus can be secured, using swing type mounting hardware and chain designed for use of human support, to a door frame or the like for full adjustability of the height of the apparatus. Alternatively, suitable and verified sturdy chairs can be employed in several possible ways previously described to effect the use of the portable apparatus of the present invention. It must be realized that not all chairs are suitable, either from a strength or configuration standpoint.

Also, in one of the embodiments, the tubular member 26D can be supported by the beam 60C. However, in order to adjust the height of the apparatus, the tubular member 26D and attached beam 60C can be rotated through 180 degrees so that the height location 76 and 78 of the apparatus relative to the supporting chairs 87 and 88 can be varied.

A working height of about waist level is desirable for the full benefit of the adjustment potential. However, the good control available with, for example, the back to back chair deployment, FIG. 1 or FIG. 3 or the deployment of FIG. 4 is preferred for many less agile users and most of the benefit is available as such. These are the preferred deployments for new users.

By disposing, in the case of a lower back adjustment, the abdomen, or, in the case of a cervical adjustment, either the posterior or lateral neck region, of the user between the convex support/arcuate fulcrum and the spinal column, as the body is curved about the axis of the support, based on the influence of the unsupported body regions, a radial resistance pressure acts on the spine of the user. This pressure or movement tends to urge the vertebrae adjacent to the body region adjacent to the arcuate fulcrum to a position of maximum separation relative to vertebrae on either side. This separation is ultimately limited to the natural constraint imposed by the facet joints, ligaments and cartilage of the spinal column.

More specifically, with respect to cervical adjustment, the method disclosed in this case is based on the principle of utilizing the combined effect of gravity, leverage, and the arch to adjust the human cervical spinal. The method is defined as a user, whose primary body weight is basically fully supported in either a supine or related lateral position on a horizontal plane substantially rigid surface, providing an elongate member defining a substantially convex substantially rigid surface featuring a radius of about 3 inches, upon which the user transversely positions and supports either a dorsal neck region or a lateral neck region such that the head of the user is at the opposite side of the manifest arcuate fulcrum and unsupported, at which time the user dictates a suitable movement of rotation to the head, whereby, under the influence of gravity acting on the unsupported head region of the user, the arcuate fulcrum provides extensively reducing resistance and path to the unsupported side such that adjacent vertebrae of the user's spine are directed radially and extensively along the neck region so divergently supported, thus effecting cervical adjustment.

The present invention provides a unique and low cost portable apparatus and method for enabling a user thereof to adjust the user's spine.

What is claimed is:

1. A portable spinal adjustment apparatus for assisting a user to adjust the user's spine, said apparatus combined with an independent support in deployment, said independent support including but not limited to chairs, stools, saw horses, chain and rope, said apparatus comprising:
    an elongate member having a first end and a second end,
    said elongate member defining a greatest dimension a substantially rigid substantially convex surface disposed between said first end and said second end of said elongate member,
    said elongate member shape selected from the group consisting of tubular, semi-circular and inverted U-shaped,
    said substantially rigid substantially convex surface defining a radius of about two to four inches for suitable spine-adjusting opposition pressure,
    said first end and said second end of said elongate member defining means to engage said independent support for safe and convenient deployment,
    said means to engage being selected from the group consisting of padding, deformable plastics, rubber, and stops for adherence and/or fixation and/or non-marring with respect to said independent support,
    said first end of said elongate member engaging said independent support and said second end of said elongate member engaging said independent support such that said substantially rigid substantially convex surface is horizontal and sufficient to transversely communicate with and contact an abdominal region of the user,
    said elongate member and said independent support in combination manifesting an arcuate fulcrum whereby in use of the apparatus, due to gravity acting on unsupported body regions of the user, said arcuate fulcrum exerts a spine-adjusting pressure to the supported body region such that adjacent vertebrae of the user's spine are urged radially and extensively along the supported body region for relieving pressure on adjacent discs.

2. A portable spinal adjustment apparatus as set forth in claim 1 further including:
    indicia visible on a convenient surface of said elongate member, said indicia include pictographs recognizable throughout the world, and connected in sequence, as to some how the apparatus is to be used and further pictographs showing some how the apparatus is not to be used.

3. A portable spinal adjustment apparatus as set forth in claim 1 wherein said apparatus further includes:
    a beam of rectangular cross sectional configuration, such that said beam defines a first and a second flat and a first and a second border, said beam extends along and is rigidly secured to an inside surface of said elongate member, said first border of said beam secured to said inside surface of said elongate member and said second border of said beam secured to said inside surface of said elongate member; wherein
    said beam having a first extremity and a second extremity, the arrangement is such that said first extremity of said beam projects away from said first end of said elongate member and said second extremity of said beam projects away from said second end of said elongate member.

4. A portable spinal adjustment apparatus as set forth in claim 3 wherein
    said beam is secured to said tubular elongate member such that said first flat and said second flat each define a distinct chord which extends internally within and across said tubular elongate member, the arrangement being such that when said beam is supported at said first flat of said beam, said tubular elongate member is disposed in a first location thereof and when said beam is supported at said second flat of said beam, said tubular elongate member is disposed in a second location thereof, said second location differing in elevation from said first location.

5. A portable spinal adjustment apparatus as set forth in claim 1 further including:
    said elongate member having an attached finish selected from the group consisting of resilient and textured.

6. A portable spinal adjustment apparatus as set forth in claim 1 wherein
    stop means are selected from the group consisting of boosts and indentations.

7. A portable spinal adjustment apparatus for assisting a user to adjust the user's spine, said apparatus combined with an independent support in deployment, said independent support including but not limited to chairs, stools, saw horses, chain and rope, said apparatus comprising:
    an elongate member having a first end and a second end and extending between said first end and said second end, a first edge and a second edge,
    said elongate member defining a substantially rigid substantially convex surface disposed between said first end and said second end bounded by said first edge and said second edge of said elongate member,
    said substantially rigid substantially convex surface defining a length sufficient to contact a user's abdomen and a radius of about two to four inches for suitable, safe yet extensively resisting the user's body weight,
    said elongate member further defining an inside surface, convenient and extending concavely, between the first and second edges, adjacent the convex surface,
    said first end and said second end and said first edge and said second edge of said elongate member defining means of engagement for safe and convenient deployment with respect to said independent support, such that in variations of deployment involving engagement at said ends or said edges, or said inside surface of said elongate member in combination with said independent support, said rigid convex surface is upward and horizontal and sufficient to transversely communicate with and support a body region of the user and said combination manifesting an arcuate fulcrum, so that in use of said apparatus, due to gravity acting on an unsupported body region of the user, said arcuate fulcrum exerts a spine-adjusting pressure to the supported body region such that adjacent vertebrae of the user's spine are urged radially and extensively along the supported body region for relieving pressure on adjacent discs.

8. A portable spinal adjustment apparatus as set forth in claim 7 wherein
said means of engagement is selected from the group consisting of resilient coverings, paddings, deformable plastics, rubber, and stops for the purpose of adherence and/or fixation and/or non-marring and/or elevation adjustment with respect to independent support.

9. A portable spinal adjustment apparatus as set forth in claim 8 wherein
said stops being indicated and defined by elongate member contour offering opposition with respect to independent support.

10. A portable spinal adjustment apparatus as set forth in claim 3 further including:
a first hole and a second hole, respectively, in said first extremity and said second extremity of said beam;
said first hole and said second hole offering engagement of said beam to independent support.

11. A portable spinal adjustment apparatus as set forth in claim 1 wherein
said elongate member is generically comprised of a first kitchen chair and a second kitchen chair, a separation padding and a shape padding; wherein
the arrangement being such that the first and second chairs, each defining an elongate substantially rigid member at the top of the chair backs are disposed back to back, each thus being independent support for the other, with said separation padding as means of engagement with independent support, and said shape padding combined with the rigid members and separation padding defining said substantially convex surface.

12. A spinal adjustment method for assisting a user to adjust the user's lumbar spine according to claim 1, said method steps comprising:
providing an elongate member, an independent support and means for engagement;
said independent support consisting of two chairs each having a front seat side and a rear elevated back side;
arranging the rear elevated sides of said chairs back to back and in a position whereby said means for engagement is positioned between and on a top surface of the elevated sides of said chairs thereby providing said elongate member;
kneeling on said front seat side of either chair and transversely positioning and supporting an abdominal region on said elongate member such that the user's upper torso is at the opposite side of the back to back arrangement of said chairs;
transferring the user's body weight from the knees to the abdomen so supported on said elongate member;
relaxing for a suitable moment;
wherein under the influence of gravity acting on unsupported body regions of the user, the elongate member, manifesting an arcuate fulcrum, provides extensively reducing resistance and path to the user's anatomy so divergently supported such that adjacent vertebrae of the user's spine are directed radially and extensively along the abdominal region, thus effecting lumbar adjustment.

* * * * *